(12) United States Patent
Park et al.

(10) Patent No.: US 7,183,056 B2
(45) Date of Patent: Feb. 27, 2007

(54) METHOD FOR PERFORMING MULTIPLEX PCR WITH CYCLIC CHANGES OF PCR PARAMETERS

(75) Inventors: Se Ho Park, Daejon-Shi (KR); Hae Sik Yang, Daejon-Shi (KR); Dae Sik Lee, Daejon-Shi (KR); Yong Beom Shin, Daejon-Shi (KR); Kyu Won Kim, Daejon-Shi (KR); Tae Hwan Yoon, Gyeonggi-Do (KR); Sung Jin Kim, Daejon-Shi (KR); Yun Tae Kim, Daejon-Shi (KR)

(73) Assignee: Electronics and Telecommunications Research Institute, Daejon-shi (KR)

( * ) Notice: Subject to any disclaimer, the term of this patent is extended or adjusted under 35 U.S.C. 154(b) by 427 days.

(21) Appl. No.: 10/697,295

(22) Filed: Oct. 31, 2003

(65) Prior Publication Data

US 2004/0146897 A1    Jul. 29, 2004

(30) Foreign Application Priority Data

Nov. 5, 2002    (KR) .................... 10-2002-0068008

(51) Int. Cl.
    *C12Q 1/68*    (2006.01)
(52) U.S. Cl. .................. 435/6; 435/91.1; 435/91.2; 536/23.1; 536/24.33
(58) Field of Classification Search ............... None
    See application file for complete search history.

(56) References Cited

U.S. PATENT DOCUMENTS 5,501,963 A * 3/1996 Burckhardt .................. 435/6
5,985,673 A   11/1999 Bao et al.
6,355,422 B1  3/2002 Liu et al.

OTHER PUBLICATIONS

Khaled et al. FEMS Microbiology Letters vol. 153:191-197. 1997.*

Henegariu et al.; "Multiplex PCR: Critical Parameters and Step-by-Step Protocol"; Research Reports; Sep. 1997; vol. 23; No. 3; pp. 504-511.

P. Markoulatos, et al.; *"Multiplex Polymerase Chain Reaction: A Practical Approach"*; Journal of Clinical Laboratory Analysis 16:47-51 (2002).

Panu H. Hendolin, et al.; *"Use of Multiplex PCR for Simultaneous Detection of Four Bacterial Species in Middle Ear Effusions"*; Journal of Clinical Microbiology; Nov. 1997; pp. 2854-2858.

Siva Raja, Talal El-Hefnawy, Lori A. Kelly, Melissa L. Chestney, James D. Luketich, and Tony E. Godfrey. Temperature-controlled Primer Limit for Multiplexing of Rapid, Quantitative Reverse Transcription-PCR Assays: Application to Intraoperative Cancer Diagnostics, 2002, pp. 1329.

Eggerding FA, A one-step coupled amplification and oligonucleotide ligation procedure for multiplex genetic typing., Jun. 1995, pp. 337.

* cited by examiner

*Primary Examiner*—Teresa E. Strzelecka
*Assistant Examiner*—Heather G. Calamita
(74) *Attorney, Agent, or Firm*—Mayer Brown Rowe & Maw LLP (57) ABSTRACT

The present invention is directed to an improved multiplex PCR method for obtaining at least two PCR products from one PCR solution. In the multiplex PCR method for having at least two DNA amplified products from a sample positioned in a PCR equipment, the object of the present invention is to provide a novel multiplex PCR method characterized in that a primer annealing temperature and an extension time be changed per cycle with constant periods. When a multiplex PCR is performed in accordance with the present invention, limitations in determining PCR conditions due to a various sizes of PCR products or dimers caused by primers can be eliminated, and time and efforts required for determining the PCR conditions to various samples can also be reduced. Further, not only refined DNAs like cDNA, genomic DNA, vector, etc, but blood can be directly used as a multiplex PCR sample, and PCR amplification reaction can be performed even with a sample having the smallest amounts.

5 Claims, 7 Drawing Sheets

Upper : BF5 (from genbank)
Lower : Analyzed Result of a Sequence

```
  1                           TTTTAGCAAAAGCGTCCAGAAAGGAGAGCTTAGCAG
               ---------------||||||||||||||||||||||||||||||||||||
101  CAGAATTCGCCCTTTTTTAGCAAAAGCGTCCAGAAAGGAGAGCTTAGCAG

37  GAGTCCTAGCCCTTTCACCCATACACATTTGGCTCAGGGTTACCGAAGAG
     ||||||||||||||||||||||||||||||||||||||||||||||||||
151  GAGTCCTAGCCCTTTCACCCATACACATTTGGCTCAGGGTTACCGAAGAG

87  GGGCCAAGAAATTAGAGTCCTCAGAAGAGAACTTATCTAGTGAGGATGAA
     ||||||||||||| ||||||||||||||||||||||||||||||||||||
201  GGGCCAAGAAATTAGGGTCCTCAGAAGAGAACTTATCTAGTGAGGATGAA

137  GAGCTTCCCTGCTTCCAACACTTGTTATTTGGTAAAGTAAACAATATACC
     ||||||||||||||||||||||||||||||||||||||||||||||||||
251  GAGCTTCCCTGCTTCCAACACTTGTTATTTGGTAAAGTAAACAATATACC

187  TTCTCAGTCTACTAGGCATAGCACCGTTGCTACCG
     |||||||||||||||||||||||||||||||||||---------------
301  TTCTCAGTCTACTAGGCATAGCACCGTTGCTACCGAAGGGCGAATTCCAG
```

FIG. 3B

Upper : P5 (from genbank)
Lower : Analyzed Result of a Sequence

```
1                                         TTTGAATTTACTCAGTTT
   -----------------------------------    ||||||||||||||||||
51 TAACGGCCGCCAGTGTGCTGGAATTCGCCCTTTTTGAATTTACTCAGTTT

19  AGAAAACCAAGCTACATATTGCAGAAGAGTACATTTGAAGTGCCTGAAAA
    ||||||||||||||||||||||||||||||||||||||||||||||||||
100 AGAAAACCAAGCTACATATTGCAGAAGAGTACATTTGAAGTGCCTGAAAA

69  CCAGATGACTATCTTAAAGACCACTTCTGAGGAATGCAGAGATGCTGATC
    ||||||||||||||||||||||||||||||||||||||||||||||||||
150 CCAGATGACTATCTTAAAGACCACTTCTGAGGAATGCAGAGATGCTGATC

119 TTCATGTCATAATGAATGCCCCATCGATTGGTCAGGTAGACAGCAGCAAG
    ||||||||||||||||||||||||||||||||||||||||||||||||||
200 TTCATGTCATAATGAATGCCCCATCGATTGGTCAGGTAGACAGCAGCAAG

169 CAATTTGAAGGTACAGTTGAAATTAAACGGAAGTTTGCTGGCCTGTTGAA
    ||||||||||||||||||||||||||||||||||||||||||||||||||
250 CAATTTGAAGGTACAGTTGAAATTAAACGGAAGTTTGCTGGCCTGTTGAA

219 AAATGACTGTAACAAAAGTGCTTCTGGTTATTTAACAGATGAAAATGAAG
    ||||||||||||||||||||||||||||||||||||||||||||||||||
300 AAATGACTGTAACAAAAGTGCTTCTGGTTATTTAACAGATGAAAATGAAG

269 TGGGGTTTAGGGGCTTTTATTCTGCTCATGGCACAAAACTGAATGTTTC
    |||||||||||||||||||||||||||||||||||||||||||||||||
350 TGGGGTTTAGGGGCTTTTATTCTGCTCATGGCACAAAACTGAATGTTTC
```

FIG. 3C

Upper : BF8 (from genbank)
Lower : Analyzed Result of a Sequence

```
  1             GTCCAATTTCAAATCACAGTTTTGGAGGTAGCTTCAGA
     ------------||||||||||||||||||||||||||||||||||||||
  1  GAATTCGCCCTTGTCCAATTTCAAATCACAGTTTTGGAGGTAGCTTCAGA

39  ACAGCTTCAAATAAGGAAATCAAGCTCTCTGAACATAACATTAAGAAGAG
     ||||||||||||||||||||||||||||||||||||||||||||||||||
 51  ACAGCTTCAAATAAGGAAATCAAGCTCTCTGAACATAACATTAAGAAGAG

89  CAAAATGTTCTTCAAAGATATTGAAGAACAATATCCTACTAGTTTAGCTT
     ||||||||||||||||||||||||||||||||||||||||||||||||||
101  CAAAATGTTCTTCAAAGATATTGAAGAACAATATCCTACTAGTTTAGCTT

139  GTGTTGAAATTGTAAATACCTTGGCATTAGATAATCAAAAGAAACTGAGC
     ||||||||||||||||||||||||||||||||||||||||||||||||||
151  GTGTTGAAATTGTAAATACCTTGGCATTAGATAATCAAAAGAAACTGAGC

189  AAGCCTCAGTCAATTAATACTGTATCTGCACATTTACAGAGTAGTGTAGT
     ||||||||||||||||||||||||||||||||||||||||||||||||||
201  AAGCCTCAGTCAATTAATACTGTATCTGCACATTTACAGAGTAGTGTAGT

239  TGTTTCTGATTGTAAAAATAGTCATATAACCCCTCAGATGTTATTTTCCA
     ||||||||||||||||||||||||||||||||||||||||||||||||||
251  TGTTTCTGATTGTAAAAATAGTCATATAACCCCTCAGATGTTATTTTCCA

289  AGCAGGATTTTAATTCAAACCATAATTTAACACCTAGCCAAAAGGCAGAA
     ||||||||||||||||||||||||||||||||||||||||||||||||||
301  AGCAGGATTTTAATTCAAACCATAATTTAACACCTAGCCAAAAGGCAGAA

339  ATTACAGAACTTTCTACTATATTAGAAGAATCAGGAAGTCAGTTT GAAT
     |||||||||||||||||||||||||||||||||||||||||||||-||||
351  ATTACAGAACTTTCTACTATATTAGAAGAATCAGGAAGTCAGTTTTGAAT

389  TTACTCAGTTTAGAAAACCAAGCTACATATTGCAGAAGAGTACATTTGAA
     ||||||||||||||||||||||||||||||||||||||||||||||||||
401  TTACTCAGTTTAGAAAACCAAGCTACATATTGCAGAAGAGTACATTTGAA

438  GTGCCTGAAAACCAGATGACTATCTTAAAGA
     ||||||||||-||||||||||||||||||||-------------------
451  GTGCCTGAAA CCAGATGACTATCTTAAAGACTGTTAAGGGCGAATTC
```

FIG. 3D

Upper : P1 (from genbank)
Lower : Analyzed Result of a Sequence

```
  1 TGCTTGTGAATTTTCTGAGACGGATGTAACAAATACTGAACATCATCAAC
    ||||||||||||||||||||||||||||||||||||||||||||||||||
  1 TGCTTGTGAATTTTCTGAGACGGATGTAACAAATACTGAACATCATCAAC

51 CCAGTAATAATGATTTGAACACCACTGAGAAGCGTGCAGCTGAGAGGCAT
    ||||||||||||||||||||||||||||||||||||||||||||||||||
 51 CCAGTAATAATGATTTGAACACCACTGAGAAGCGTGCAGCTGAGAGGCAT

101 CCAGAAAAGTATCAGGGTAGTT
    |||||||| ||| ||||||||-----
101 CCAGAAAAGCATCGGGGTAGTTCTGTT
```

Unit:micrometer

METHOD FOR PERFORMING MULTIPLEX PCR WITH CYCLIC CHANGES OF PCR PARAMETERS

BACKGROUND OF THE INVENTION

1. Field of the Invention

The present invention relates to an improved method for multiplex PCR for resulting in at least two amplified DNA products from one PCR solution. In particular, the present invention relates to the novel method for performing multiplex PCR to solve the problems that size differences among many types of required amplified products can not be greatly increased, non-specific DNA amplified products are produced, and dimers caused by using at least two pairs of primers in the conventional multiplex PCR.

2. Description of the Prior Art

To perform disease diagnosis, detection and identification of pathogenic bacteria, and research on variation or abnormality of organism gene, such as SNP(single nucleotide polymorphism), STR(short tandem repeat), insertion, deletion and mutation etc, the sequence of amplified target DNA must be secured in advance. As a method for amplifying target DNA sequence, there exists PCR (polymerase chain reaction) method, SDA(strand displacement amplification) method, and ones for TMA(transcription mediated amplification), by which the target DNA is synthesized from mRNA, NASBA(nucleic acid sequence based amplification) and so on. In general applications, the PCR method is widely used for its amplification efficiency superior to other methods above.

In recent years, researches have been conducted to perform DNA amplification in a small equipment or a small chip like a lab-on-a-chip and to analyze DNAs in a short tome However, common problems of the above methods are have common problems as follows. It is complicated to purely refine genomes from blood samples or tissue samples, and various target genes must be amplified safely in a small space like chips in order to obtain information as many as possible with small costs. Multiplex PCR method have been used to obtain various DNA amplified products in a limited space.

The multiplex PCR method produces at least two amplified DNA products from one reaction solution, and at least two pairs of primers are used. Therefore, if the reaction condition and primer sequence are not appropriate, primer dimers may be produced or non-specific DNA products may be produced, or required-amplified DNA products can not be obtained. Conventional methods require a lot of times and efforts in order to find the optimal condition for amplification of different size of DNA because temperature and time conditions are fixed. For example, in the documents by Hinegariu O et al, "Multiplex PCR: critical parameters and step-by-step protocol"(Biotechniques, 1997, pp. 504–511) and by P. markoulatos et al, "Multiplex Polymerase Chain Reaction: a practical approach" (J. Clin. Lab. Anal. 2002. pp. 47–51), researches have been conducted to find the optimal multiplex PCR conditions for various combination of PCR parameters like concentration of primers, Mg++, taq DNA polymerase buffer, temperature of annealing and extension time to a specific sample. However, these conventional methods have some problems, such as, the methods require long time, much efforts and large amount of samples to optimize the PCR condition because of various combinations of PCR parameter, and the procedures should be repeated for a new samples.

SUMMARY OF THE INVENTION

Therefore, the object of the present invention is to provide a method for finding optimal multiplex PCR condition for performing simple and stable PCR.

Meanwhile, another object of the present invention is to provide the method for multiplex PCR using a sample which has been required to perform the conventional multiplex PCR, especially a diluted blood sample which has not been refined in the case of a blood sample.

To achieve the above objects, inventors of the present invention have conducted researches and have found that target DNA sequences can be amplified in simple and safe way by the multiplex PCR method of the present invention by changing annealing temperature and extension time among several parameters of the multiplex PCR per cycle having constant period.

Further, a pretreatment step of a raw sample like blood, which has been diluted by buffers and not been refined, can be directly used in a multiplex PCR, thereby a preconditioning step for obtaining refined DNAs can be eliminated.

Also, DNA can be amplified in multiplex PCR with a small amount of about 1 µl of reaction volume.

As a result of recent development in molecular biology, not only human genome sequences are completely analyzed but genome sequences of organism useful to a human being or valuable for research are subsequently analyzed and disclosed. To be meaningful and to be used by a human-being, some genes of the disclosed sequences expressing protein and function of the genes should be revealed. In recent years DNA chip related fields are developing fast to solve the above tasks. Researches are being conducted to find functions of unknown genes from gene expression patterns of patients having specific disease, or from gene expression patterns responding to stimulus from outside of a living body. Meanwhile, as the genome researches proceed, it has been found that sequences between individuals are slightly different even in the gene of which functions and sequences are disclosed. Such differences of base sequences present between individuals or species constituents are called SNP. The SNP not only causes differences of character between individuals but becomes one reason for differences of resistance and sensitiveness to drugs, and in the worst case cause of genetic diseases. Many laboratories have built SNP database from known human genomes and been making an effort to find out relationship between drug sensitiveness and disease to the SNP.

In the future, accumulated gene related information will be used in a development of DNA diagnosis equipment. For the purpose of gene diagnosis, refined genomes should be prepared from samples and DNA of interest should be amplified. These tasks become obstacles to miniaturization and speed-up of diagnosis equipment and fast speed. According to the present invention, to obtain various kinds of amplified DNA products by the multiplex PCR, blood sample is directly used for DNA amplification, and the above problems can be overcome.

The present invention performs multiplex PCR by using either of raw blood sample or refined DNA.

There exists a need for PCR equipment capable of programming adjustment of temperature and other reaction conditions for multiplex PCR. The PCR comprises steps of preliminary denaturing, denaturing, cycling (annealing and extension), and additional extension and the PCR program consists of set values of temperature and time of each step and number of cycle of the cycling step. The method for performing PCR of the present invention is achieved by adjusting the temperature and time of the annealing and extension step among program setting values as set forth below.

Annealing step: X° C., 30 seconds, wherein the annealing temperature, X° C., wherein annealing temperature is set to "a" ° C. increment per "b" cycle.

Extension step: 72° C., Y seconds, wherein the extension time is set to "c" second increment per "d" cycle.

The program setting values of the PCR, X, Y, a, b, c, and d are appropriately adjusted in accordance with the Tm of primers to be used, and the size of DNA which needs to be amplified. In particular, the adjustment is as follows.

X: set to a value lower than the lowest Tm value of the primers by 2° C.

"a" and "b" : a is basically set as value of (Tm_max–Tm_mm)/number of total cycle, b is basically 1, but in the case that the "a" value for 1 cycle is too small to set in PCR equipment, the "a" value is adjusted by changing the "b" value (i.e. the number of cycles). For example, 0.05° C. per cycle is changed to 0.2° C. per 4 cycles.

Y: this value is initially set as the time required in synthesizing DNA of the shortest size among amplified PCR products which need to be amplified and is determined as follows.

Y(sec)=Lmin/rate of DNA synthesis velocity of taq DNA polymerase (bp/sec)

In the above equation, Lmin indicates the smallest size (bp) of the PCR products, and the rate of DNA synthesis of taq DNA polymerase is determined empirically and is generally 13 bp/sec.

c (sec): this value is set as the time required for synthesizing the largest size of DNA of among amplified PCR products sufficiently at latter part of whole PCR cycles and is determined as follows.

c(sec) =[(Lmax–Lmin)/(rate of DNA synthesis velocity of taq DNA polymerase; bp/sec)]/(number of total cycles–7)

In the above equation, Lmax indicates the largest size of the PCR products, and the Lmin indicates the shortest size of the PCR products.

"d"(cycle #) is basically 1. However, in the case that value of L max–Lmin is not big so that the c value is too small to be set in the PCR equipment, this problem can be solved by changing the d(cycle) like the case of changing the "a".

Not only purified DNA (vector, genome DNA, cDNA library etc) but diluted blood can be used as samples for amplification by multiplex PCR method of present invention. If the blood is used as raw state, the PCR can not be properly performed due to proteins derived from plasma and erythrocyte. Therefore, the blood sample is prepared by dilution of 1×PCR buffer before PCR. About 1:30 (blood: buffer) is suitable as the dilution ratio, and diluted blood of 2 μl is used for 50 μl PCR. Concentrations of the other PCR elements are similar to general elements.

DESCRIPTION OF THE PREFERRED EMBODIMENTS

Hereinafter, embodiments of the present invention will be explained with reference to the accompanying drawings. Although the present invention has been described in conjunction with the preferred embodiment, the present invention is not limited to the embodiments, and it will be apparent to those skilled in the art that the present invention can be modified in variation within the scope of the invention.

First Embodiment

Multiplex PCR of Blood Sample

Among exon sequences of brca1 and brca2 of human genomes which are related to breast cancer, and ovarian cancer, when mutation is occurred in the sequences, primers listed in table 1 were used to include sequences of products include sequences with high of cancer incidence. To include, in amplified products, sequences with high cancer incidence when mutated among exon sequences of brca1 and brca2 of human genomes, which are related to breast cancer and ovarian cancer, respectively, primers listed in table 1 were used.

TABLE 1

| primer | Primer sequence | Tm (° C.) | PCR product | |
|---|---|---|---|---|
| bf9 | 5'-TTTTAGCAAAAGCGTCCAGAA-3' | 54.0 | Brca 1 exon 11 | BF5 |
| bf10 | 5'-TCGGTAGCAACGGTGCTATG-3' | 59.4 | Brca 1 exon 11 | |
| p9 | 5'-TTTGATTTACTCAGTTTAGAAAACC-3' | 55.3 | brca 2 exon 11b | P5 |
| p10 | 5'-GAAACATTCAGTTTTGTGCCCATGAGC-3' | 61.6 | brca 2 exon 11b | |
| bf15 | 5'-GTCCAATTTCAAATCACAGTTTTGGAGG-3' | 62.2 | brca 1 exon 11 | BF8 |
| bf16 | 5'-TCTTTAAGATAGTCATCTGGTTTTCAGGCA-3' | 62.7 | brca 1 exon 11 | |
| p1 | 5'-TGCTTGTGAATTTTCTGAGACGGATG-3' | 61.6 | brca 1 exon 11 | P1 |
| p2 | 5'-AACAGAACTACCCTGATACTTTTCTGGA-3' | 62.2 | brca 1 exon 11 | |

Diluted blood was used as a sample for multiplex PCR. The sample was prepared as follows.
  Total volume of PCR solution: 50 µl
  Final concentration of each element

| | |
|---|---|
| Primer concentration | 10 pmol |
| MgCl$_2$ | 2 mM |
| dNTP | 2 mM |
| 10 × PCR buffer | 5 µl |
| taq DNA polymerase | 2.5 units |
| diluted blood | 2 µl (dilution ratio - buffer:blood = 1:30) |
| pure water | up to 50 µl |

Figure 1:
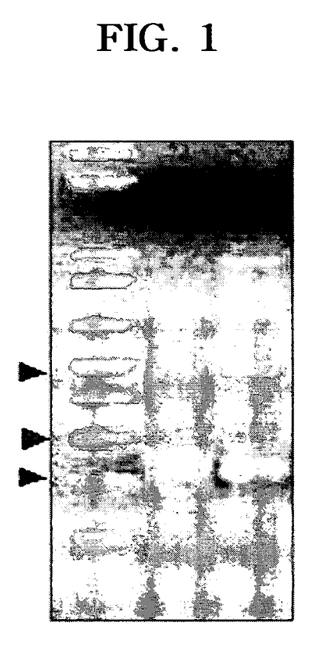
FIG. 1 shows an electrophoresis picture of multiplex PCR product using diluted blood samples in a first embodiment of the present invention. (BF8, P5, BF5, in the order of size)
Figure 3A:
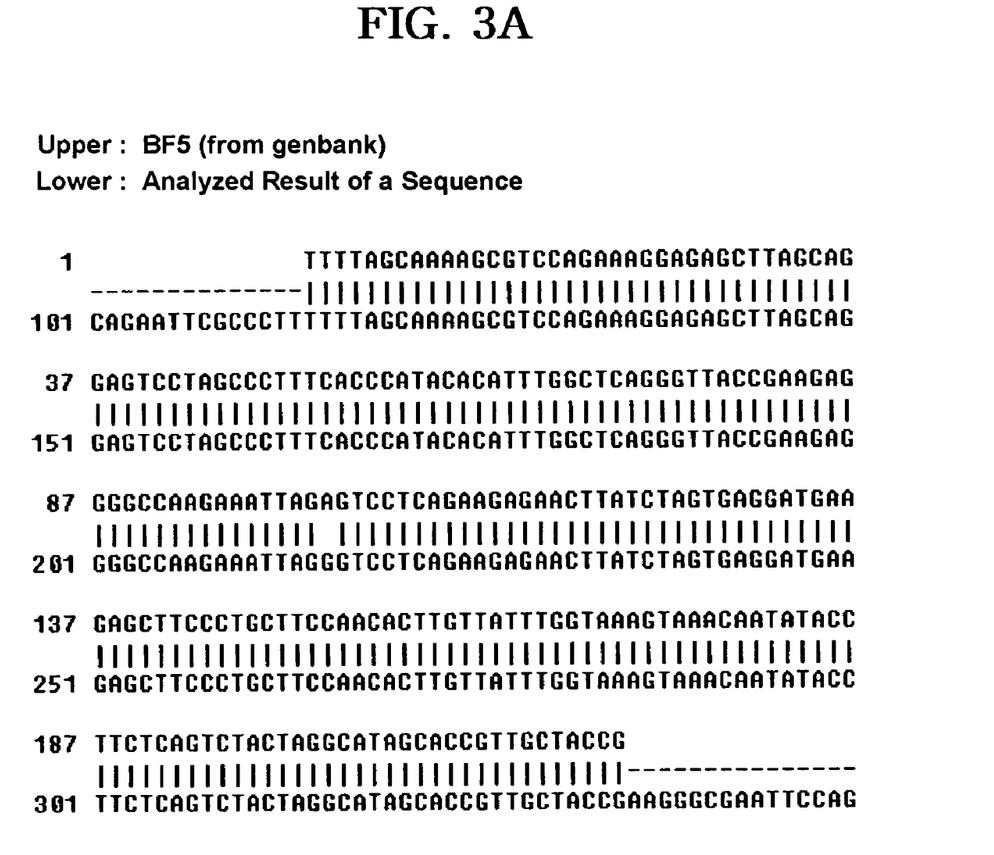
FIG. 3A shows the compared and analyzed result of a sequence of BF5 obtained from the first and second embodiments with its corresponding sequence of genbanks.

The model "icycler" made from company Bio-rad has been used as a PCR equipment. This model comprises a controller capable of programming, and the PCR parameters of the present embodiment are as follows.
  1. preliminary denaturation step: 94° C., 4 minutes
  2. cycle step
      denaturation step: 93° C., 30 seconds
      primer annealing step: 52° C., 30 seconds (0.2° C. increment per cycle)
      extension step: 72° C., 15 seconds (1 second incrmente per 3 cycles)
      40 cycles
  3. additional extension step: 72° C., 7 minutes FIG. 1 shows picture of agarose gel after EtBr(Ethidium Bromide) fluorescent treatment has been subject to, after the PCR solution amplified in the present embodiment had been subject to electrophoresis. Referring to FIG. 1, lane 1 indicates 100 bp DNA ladder, and lane 3 indicates the result from multiplex PCR performed by the above procedure. BF5, P5, and BF8 correspond from the lowest arrow to the highest arrow, respectively. Lane 2 indicates the result from multiplex PCR performed with fixed conditions of primer annealing step and extension step such as a general PCR method. PCR conditions corresponding to the lane 2 are as follows.
  1. preliminary denaturation step: 94° C., 4 minutes
  2. cycle step
      denaturation step: 93° C., 30 seconds
      primer annealing step: 55° C., 30 seconds
      extension step: 72° C., 40 seconds
      40 cycles
  3. additional extension step: 72° C., 7 minutes Identification of base sequences of the amplified products. BF5 (222 bp), P5 (317 bp), and BF8 (468 bp) from the product (i.e. lane 3 of FIG. 1) obtained in the first embodiment were separated from the agarose gel, and inserted to the Topo PCR2.1 cloning vector (made from the company, Invitrogen), and E. coli was transferred by introduction of the vector. The transformed E. coli was cultured and collected in LB(luria broth) containing dessolved, and collected, kanamycin (50 µg/ml), and each of transformed DNAs was purely refined from the E. coli, and base sequence for the DNAs was analyzed. PCR products were identified by comparing the analyzed base sequences to corresponding sequences of genbanks, and the results thereof were shown in FIG. 3A to 3C.

In the method of this embodiment wherein the diluted bloods were used as a template of multiplex PCR, the method can stay out of trouble of purely separating template DNAs, and the method of periodically changing conditions can also be more efficient than the conventional method performing PCR under fixed conditions. Even if the diluted bloods were used as a template, the remaining plasma protein and erythrocyte protein flowing during PCR treatment are obstacles to DNA amplification, so that when only leucocytes of bloods are partially refined or purely separated and subject to multiplex PCR, a better result is expected.

Second Embodiment
Multiplex PCR of Purely Refined DNA

Figure 3B:
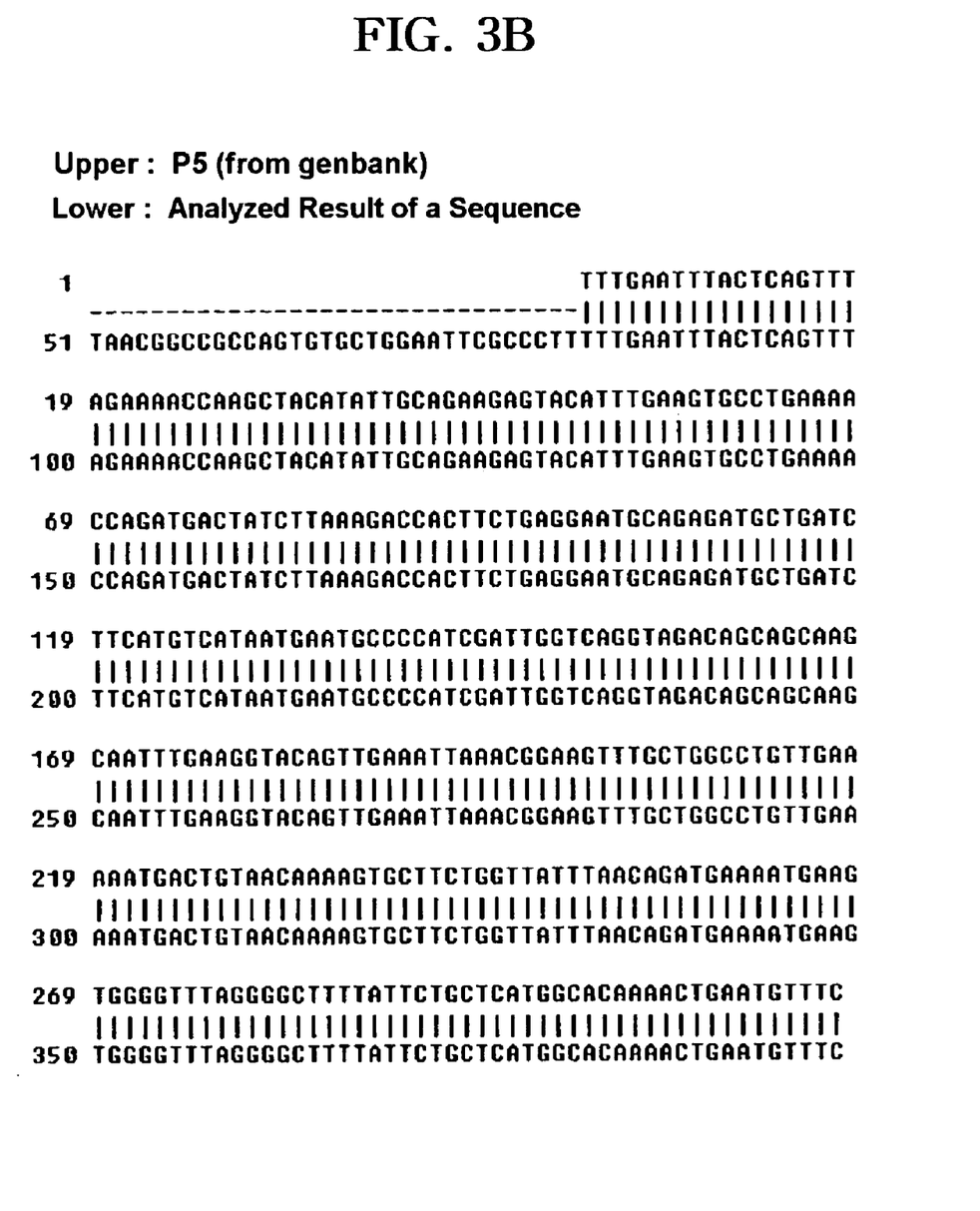
FIG. 3B shows the compared and analyzed result of a sequence of P5 obtained from the first and second embodiments with its corresponding sequence of genbanks.
Figure 3C:
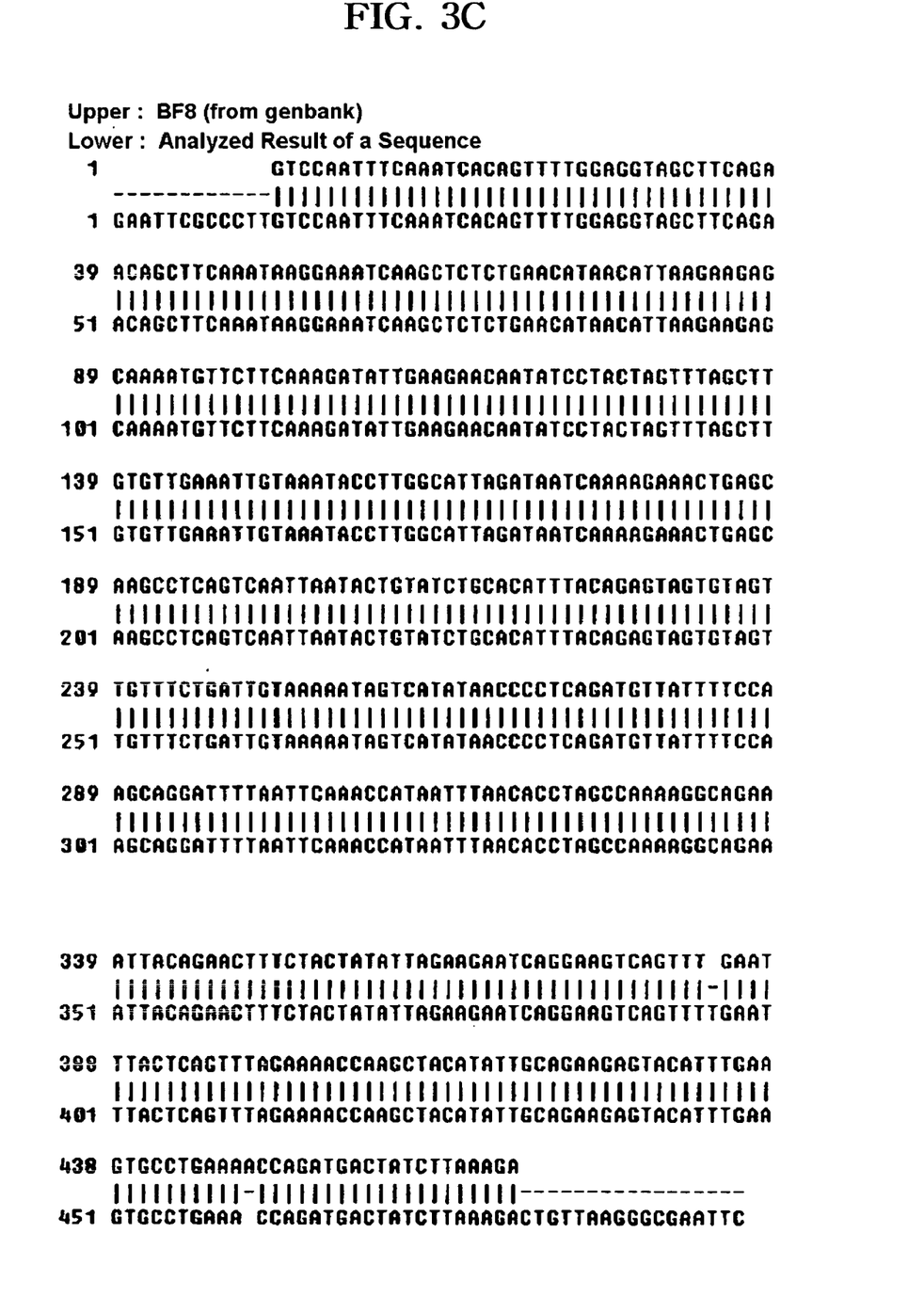
FIG. 3C shows the compared and analyzed result of a sequence of BF8 obtained from the first and second embodiments with its corresponding sequence of genbanks.
Figure 3D:
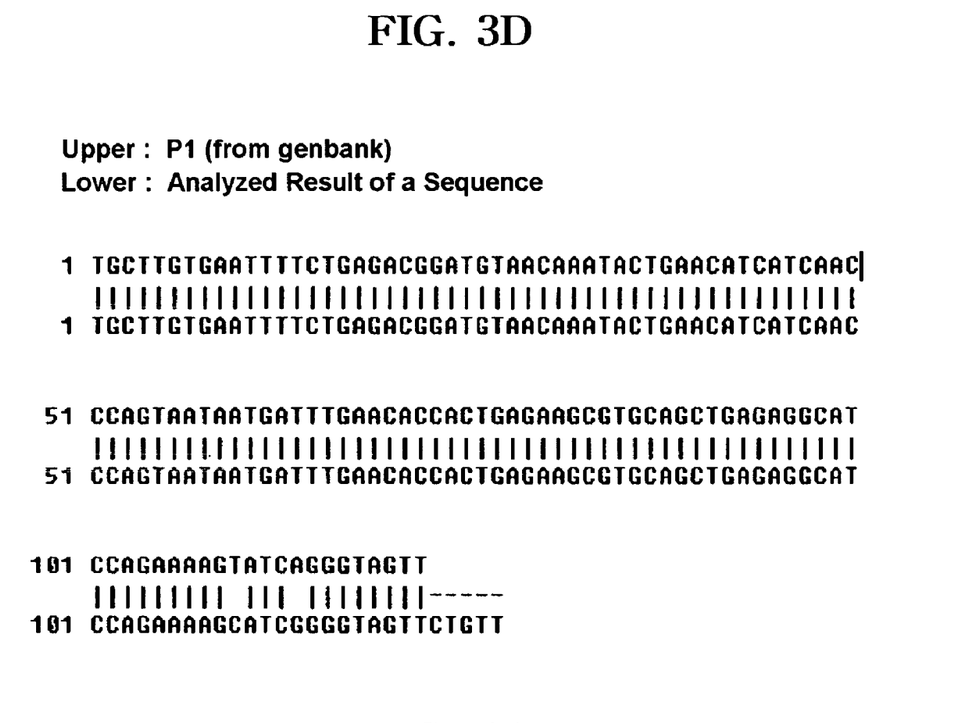
FIG. 3d shows the compared and analyzed result of a sequence of P1 obtained from the first and second embodiments with its corresponding sequence of genbanks.

P1 and P5 were respectively subject to PCR using bloods diluted by 1:30 (blood: buffer) of 1×PCR buffer. Cloning and base sequence analysis were performed with the same method as that in the first embodiment (See FIG. 3-d, 3-b).

Figure 2:
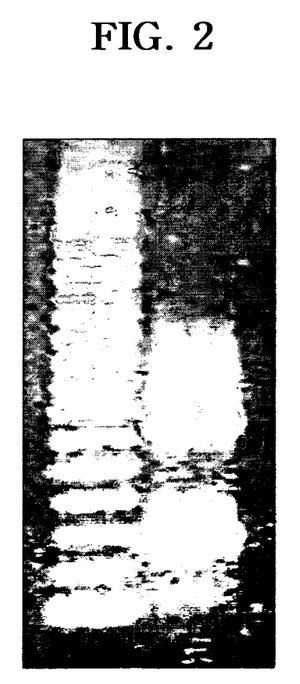
FIG. 2 shows an electrophoresis picture of multiplex PCR products performed in a second embodiment of present invention using cloned BF5 and P5 of PCR products as templates, wherein the BF5 and P5 are cloned from PCR products primarily obtained from diluted bloods.

PCR elements of the same concentration and amount as those in the first embodiment were put into one tube. Each DNA cloned with P1 and P5 was used with amount of 20 ng as a PCR template instead of diluted blood. Corresponding primer pairs were also put into the tube and finally the sterilized water was prepared by the volume of the PCR mixture to reach 50 µl. Adjustment of parameters to PCR equipment and multiplex PCR amplification reaction were performed in the same method as that in the first embodiment. The specific adjustments are as follows.
  1. preliminary denaturation step: 94° C., 4 minutes
  2. cycle step
      denaturation step: 93° C., 30 seconds
      primer annealing step: 53° C., 30 seconds (0.2° C. increment per cycle)

extension step: 72° C., 15 seconds (1 second increment per 3 cycles)
35 cycles
3. additional extension step: 72° C., 7 minutes FIG. 2 shows the electrophoresis picture of multiplex PCR products of P1 and P5 amplified in this embodiment. In FIG. 2, lane 1 indicates the 50 bp DNA marker, and lane 2 indicates the P1 and P5 which has been subject to multiplex PCR. The lower band among the two DNA bands is P1 (127 bp) and the upper one is P5 (317 bp).

Also, as performed in the first embodiment, P1 and P5 were purely separated and cloned, and then E. coli was transferred by introducing the vector. The transformed E. coli was then cultured and base sequence was analyzed. PCR products were identified by comparing the analyzed base sequences to its corresponding sequences within genbanks, and the results thereof were shown in FIG. 3B(i.e. result of base sequence analysis of P5) and 3d(i.e. result of base sequence analysis of P1).

In this embodiment, PCR parameters were set in accordance with the method of the present invention, and multiplex PCR was performed one time, thereby performing multiplex PCR for two DNAs could be successfully achieved. However, by using refined DNA as a multiplex PCR template, a clearer result was obtained than by using diluted blood.

Third Embodiment
Performing Micro Multiplex PCR in a Silicon Chamber

A revised quadranglar pyramid chamber of 0.2 µl volume was made by KOH wet etching on a silicon wafer, and silicon oxides were deposited thereon by CVD (chemical vapor deposition) to make the surface thereof hydrophilic. 50 µl of PCR mixture like that in the second embodiment was made with, and 0.2 µl of the mixture was charged into the chamber and mineral oil was also put to cover the surface thereof so that the evaporation be prevented. However, 1×SYBR green I fluorescent destain material was contained in the PCR mixture. As the SYBR green I strongly emits fluorescence only when it is within the DNA of double chains, PCR amplification result can be verified. Therefore, when the PCR amplification is not under proper performance, the fluorescence becomes unclear.

As a negative control, a sample was prepared from PCR mixture having all the same elements except a template DNA(i.e. vector DNA of which the P1 or P5 has been cloned).

Two silicon oxide chambers prepared as described above were mounted on the upper side of the PCR tube hole of the PCR equipment (icycler from Bio-rad company), and then PCR was performed.

PCR conditions are set as below. As the thermal conductivity of the silicon material is higher than that of the PCR tube material, time adjustment of each step was set shorter.
1. preliminary denaturation step: 94° C., 4 minutes
2. cycle step
   denaturation step: 93° C., 15 seconds
   primer annealing step: 53° C., 15 seconds (0.2° C. increment per cycle)
   extension step: 72° C., 15 seconds (1 second increment per 3 cycles)
   35 cycles
3. additional extension step: 72° C., 3 minutes The result of micro PCR was confirmed by the fluorescent microscope, and is shown in FIGS. 4A and 4B.

Figure 4A:
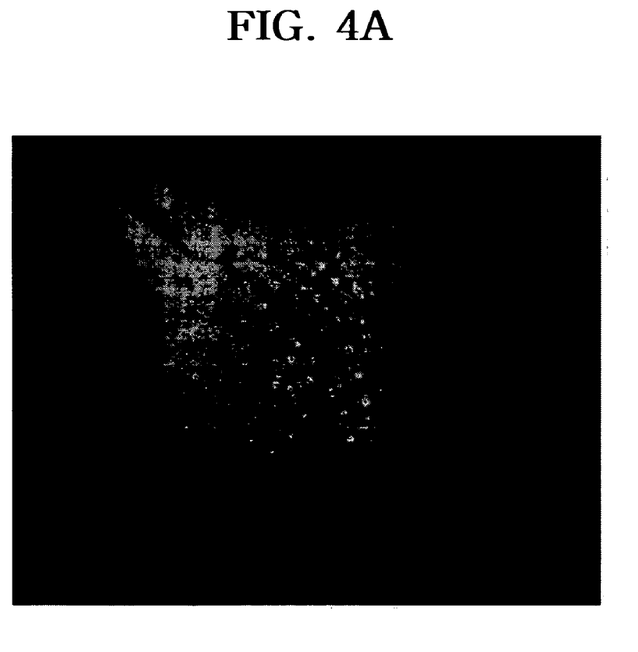
FIG. 4A shows the picture of a fluorescent microscope for the P1 and P5 after performing a micro multiplex PCR in a silicon oxide chamber of a third embodiment.
Figure 4B:
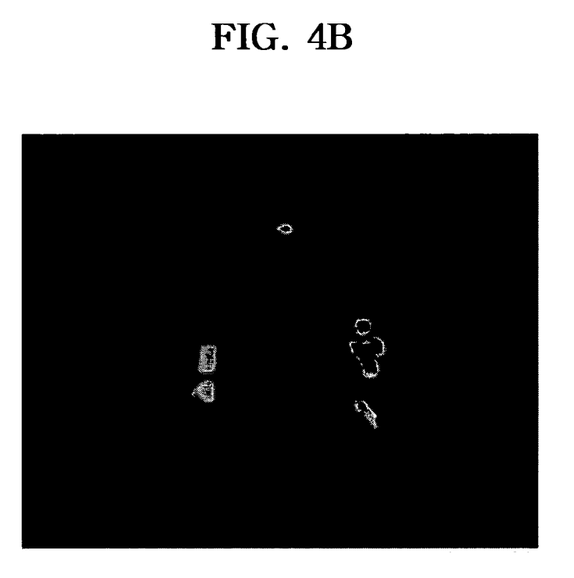
FIG. 4B shows the picture taken of a fluorescent microscope after performing a micro multiplex PCR without P1 and P5 template DNAs in a silicon oxide chamber of the third embodiment negative control.
Figure 5:
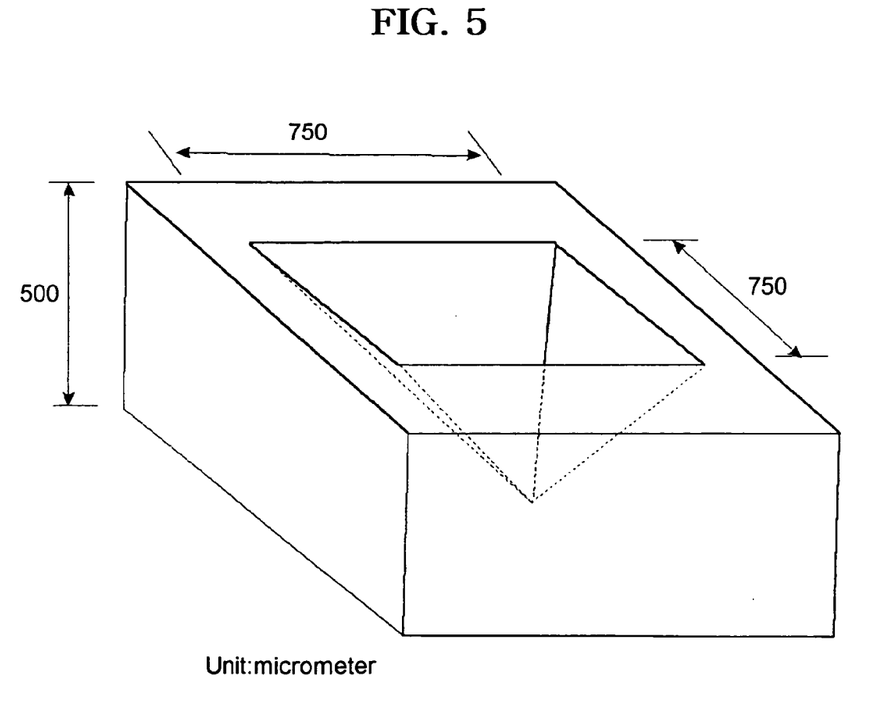
FIG. 5 shows a dimension of silicon oxide chamber used in the third embodiment.

FIG. 4A shows the result of multiplex PCR of P1 and P5 performed in a 0.2 µl silicon chamber, and FIG. 4B shows the result of negative control (i.e. multiplex PCR performed without a template). The fluorescence is barely seen in FIG. 4A, while it is strongly seen in FIG. 4A. Therefore, the multiplex PCR according to the method of the present invention can be successfully performed even with a sample having a small amount of 0.2 µl. Also, successful and normal PCR performance with small amounts of sample according to the present invention enables it useful to reduce the size of DNA amplification part within a gene diagnosis equipment.

Fourth Embodiment
Performing Micro Multiplex PCR in a Silicon Chamber (2)

In a silicon chamber of 1 µl, using genomic DNA as a template, a portion of breast cancer genome(brca1) including SNP was amplified by multiplex PCR, as in third Embodiment. The characteristics of primers used in these amplifications and PCR products were summarized in table 2.

TABLE 2

| Primer | Primer Sequence | Tm (° C.) | PCR Product (length) |
|---|---|---|---|
| br3 | 5'-6-fam-tccaagtacagtgagcacaattagcc | 58 | BR2 |
| br4 | 5'-tggagcccacttcattagtactgg | 57 | (112base) |
| br5 | 5'-6-fam-ttgttctgagacacctgatgacctg | 55 | BR3 |
| br6 | 5'-tgtgtatgggtgaaagggctagg | 58 | (156base) |
| br7 | 5'-6-fam-tccaagtacagtgagcacaattagcc | 59 | BR4 |
| br8 | 5'-tggccctctgtttcttacctagttctg | 62 | (178base) |

The primers were synthesized by adding a fluorescent material, 6-fam, at the 5'-terminal of forward primer.

Figure 6A:
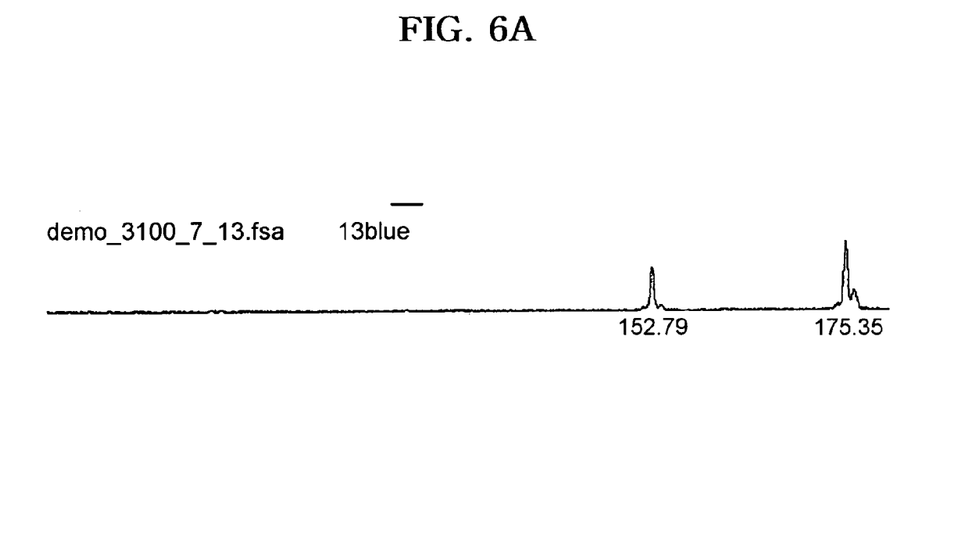
FIG. 6A shows a CE (capillary electrophoresis) result of BR3 and BR4, amplified PCR products in a silicon oxide chamber of the fourth embodiment.
Figure 6B:
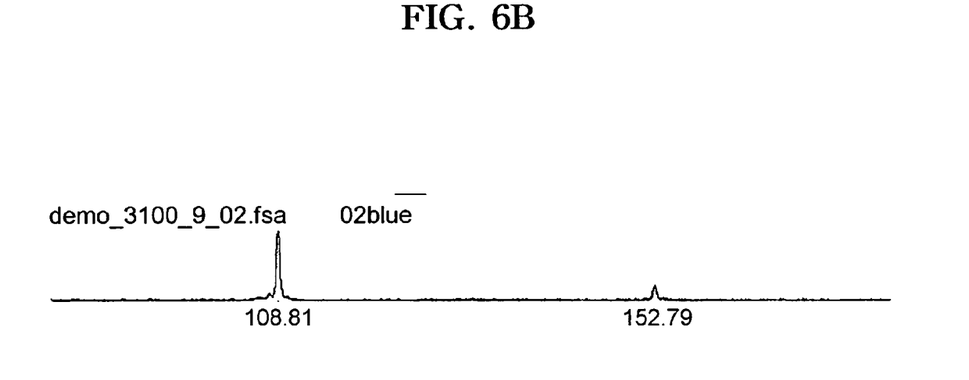
FIG. 6B shows a CE result of BR2 and BR3 amplified PCR products in a silicon oxide chamber of the fourth embodiment.

The sequence of each amplified PCR product was determined by sequence analysis. The amplified PCR products were analysed by CE (capillary electrophoresis, ABI3700) and the results were depicted in FIG. 6a and 6b. FIG. 6a is corresponding to BR3 and BR4, and FIG. 6b is corresponding to BR2 and BR3.

The amplification condition for FIG. 6a is set forth below.
Preliminary denaturation: 93° C., 2 minute and 30 seconds
Denaturation: 93° C., 20 seconds
Primer Annealing: 53° C., increased by 1° C./5 cycles
Extension: 72° C., 12 seconds, increased by 0.3 seconds/5 cycles 35 cycles
Additional Extension: 72° C., 7 minutes The amplification condition for FIG. 6b is set forth below.
Preliminary denaturation: 93° C., 2 minute and 30 seconds
Denaturation: 93° C., 20 seconds
Primer Annealing: 53° C., increased by 1° C./12 cycles
Extension: 72° C., 8 seconds, increased by 0.9 seconds/7 cycles 35 cycles
Additional Extension: 72° C., 7 minutes In the results of every CE analysis, the length of amplified PCR products are slightly different from the expected length. The differences were caused by instrumental errors.

As described above, by changing the primer annealing temperature and extension time periodically, production of dimers from primers, and of non-specific product which has been the problems of conventional multiplex PCR can be prevented, and the PCR product can be obtained in shorter time by the method of present invention comparing to the conventional method wherein the optimal considerations of multiplex PCR were found by changing con. The multiplex products could be obtained in easier way by properly adjusting the increment or decrement of annealing temperature and extension time periodically.

Furthermore, the blood sample can be amplified through multiplex PCR in accordance with the present invention without refinement. Also, the multiplex PCR method of the present invention can be performed the PCR even with small amounts of sample less than 1 μl, so that the method enables it useful to use in the DNA diagnosis chip like lab-on-a-chip by which various PCR products should be obtained and analyzed in a small space.

---

What is claimed is:

1. A method for performing multiplex PCR for having at least two amplified DNA products from samples positioned within a PCR equipment, characterized in that the primer annealing temperature and extension time are changed by a constant amount per constant number of cycles, wherein said annealing temperature increase by a value of ((Tm_max−Tm_min)/number of total cycles) per cycle, wherein said Tm_max indicates the highest melting temperature among all the primers and said TM_min indicates the lowest melting temperature among all the primers, and said extension time increases by value((Lmax−Lmin)/(rate of DNA synthesis of tag DNA polymerase: bp/sec))/(number of total cycles−7) per cycle, wherein said Lmax indicates the size of the largest PCR product, and said Lmin indicates the size of the shortest PCR product.

2. The method in claim 1,
wherein said samples are blood plasma, proto DNA (vector), CDNA library, genome, or cellular tissue including genome.

3. The method in claim 2,
wherein said samples are dilutod.

4. The method as set forth in claim 1,
wherein said PCR equipment can change the primer annealing temperature and extension time by a constant amount per constant number of cycles.

5. The method as set forth in claim 3,
wherein said diluted samples each has a volume of less than 1μL.

* * * * *

SEQUENCE LISTING

<160> NUMBER OF SEQ ID NOS: 8

<210> SEQ ID NO 1
<211> LENGTH: 221
<212> TYPE: DNA
<213> ORGANISM: Homo sapiens
<220> FEATURE:
<221> NAME/KEY: brca1 exon11b
<222> LOCATION: (1)..(221)
<223> OTHER INFORMATION: part of the sequence, human brca1 exon11b from
      genbank

<400> SEQUENCE: 1
ttttagcaaa agcgtccaga aaggagagct tagcaggagt cctagccctt tcacccatac     60
acatttggct cagggttacc gaagaggggc caagaaatta gagtcctcag aagagaactt   120
atctagtgag gatgaagagc ttccctgctt ccaacacttg ttatttggta aagtaaacaa   180
tataccttct cagtctacta ggcatagcac cgttgctacc g                       221

<210> SEQ ID NO 2
<211> LENGTH: 250
<212> TYPE: DNA
<213> ORGANISM: Homo sapiens
<220> FEATURE:
<221> NAME/KEY: brca1 exon11b
<222> LOCATION: (15)..(236)
<223> OTHER INFORMATION: PCR product of human brca exon11b from blood
      genomic DNA

<400> SEQUENCE: 2
cagaattcgc cctttttag caaaagcgtc cagaaaggag agcttagcag gagtcctagc     60
cctttcaccc atacacattt ggctcagggt taccgaagag gggccaagaa attagggtcc   120
tcagaagaga acttatctag tgaggatgaa gagcttccct gcttccaaca cttgttattt   180
ggtaaagtaa acaatatacc ttctcagtct actaggcata gcaccgttgc taccgaaggg   240
cgaattccag                                                         250

<210> SEQ ID NO 3
<211> LENGTH: 317
<212> TYPE: DNA
<213> ORGANISM: Homo sapiens
<220> FEATURE:
<221> NAME/KEY: brca2 exon11
<222> LOCATION: (1)..(317)
<223> OTHER INFORMATION: DNA sequence , part of brca2 gene exon11 from
      genbank source.

<400> SEQUENCE: 3
tttgaattta ctcagtttag aaaaccaagc tacatattgc agaagagtac atttgaagtg     60
cctgaaaacc agatgactat cttaaagacc acttctgagg aatgcagaga tgctgatctt   120
catgtcataa tgaatgcccc atcgattggt caggtagaca gcagcaagca atttgaaggt   180
acagttgaaa ttaaacggaa gtttgctggc ctgttgaaaa atgactgtaa caaaagtgct   240
tctggttatt taacagatga aaatgaagtg gggtttaggg gcttttattc tgctcatggc   300
acaaaactga atgtttc                                                 317

<210> SEQ ID NO 4
<211> LENGTH: 349
<212> TYPE: DNA
<213> ORGANISM: Homo sapiens
<220> FEATURE:
<221> NAME/KEY: human brca2 exon11
<222> LOCATION: (33)..(349)
<223> OTHER INFORMATION: PCR product sequence ,part of human brca2 exon11 from human blood genomic DNA

<400> SEQUENCE: 4

| | | | | | |
|---|---|---|---|---|---|
| taacggccgc | cagtgtgctg | gaattcgccc | tttttgaatt | tactcagttt | agaaaaccaa | 60 |
| gctacatatt | gcagaagagt | acatttgaag | tgcctgaaaa | ccagatgact | atcttaaaga | 120 |
| ccacttctga | ggaatgcaga | gatgctgatc | ttcatgtcat | aatgaatgcc | ccatcgattg | 180 |
| gtcaggtaga | cagcagcaag | caatttgaag | gtacagttga | aattaaacgg | aagtttgctg | 240 |
| gcctgttgaa | aaatgactgt | aacaaaagtg | cttctggtta | tttaacagat | gaaaatgaag | 300 |
| tggggtttag | gggcttttat | tctgctcatg | gcacaaaact | gaatgtttc | | 349 |

<210> SEQ ID NO 5
<211> LENGTH: 468
<212> TYPE: DNA
<213> ORGANISM: Homo sapiens
<220> FEATURE:
<221> NAME/KEY: human brca1 exon11
<222> LOCATION: (1)..(468)
<223> OTHER INFORMATION: part of human brca1 exon11 DNA sequence from genbank.

<400> SEQUENCE: 5

| | | | | | |
|---|---|---|---|---|---|
| gtccaatttc | aaatcacagt | tttggaggta | gcttcagaac | agcttcaaat | aaggaaatca | 60 |
| agctctctga | acataacatt | aagaagagca | aaatgttctt | caaagatatt | gaagaacaat | 120 |
| atcctactag | tttagcttgt | gttgaaattg | taaataccct | tggcattaga | taatcaaaga | 180 |
| aactgagcaa | gcctcagtca | ttaatactg | tatctgcaca | tttacagagt | agtgtagttg | 240 |
| tttctgattg | taaaaatagt | catataaccc | ctcagatgtt | attttccaag | caggatttta | 300 |
| attcaaacca | taatttaaca | cctagccaaa | aggcagaaat | tacagaactt | ctactatat | 360 |
| tagaagaatc | aggaagtcag | tttgaattta | ctcagtttag | aaaaccaagc | tacatattgc | 420 |
| agaagagtac | atttgaagtg | cctgaaaacc | agatgactat | cttaaaga | | 468 |

<210> SEQ ID NO 6
<211> LENGTH: 497
<212> TYPE: DNA
<213> ORGANISM: Homo sapiens
<220> FEATURE:
<221> NAME/KEY: human brca1 exon11
<222> LOCATION: (13)..(480)
<223> OTHER INFORMATION: PCR product sequence, part of human brca1 exon11 from human blood genomic DNA.

<400> SEQUENCE: 6

| | | | | | |
|---|---|---|---|---|---|
| gaattcgccc | ttgtccaatt | tcaaatcaca | gttttggagg | tagcttcaga | acagcttcaa | 60 |
| ataaggaaat | caagctctct | gaacataaca | ttaagaagag | caaaatgttc | ttcaaagata | 120 |
| ttgaagaaca | atatcctact | agtttagctt | gtgttgaaat | tgtaaatacc | ttggcattag | 180 |
| ataatcaaaa | gaaactgagc | aagcctcagt | caattaatac | tgtatctgca | catttacaga | 240 |
| gtagtgtagt | tgtttctgat | tgtaaaaata | gtcatataac | ccctcagatg | ttattttcca | 300 |
| agcaggattt | taattcaaac | cataatttaa | cacctagcca | aaaggcagaa | attacagaac | 360 |

```
tttctactat attagaagaa tcaggaagtc agttttgaat ttactcagtt tagaaaacca        420
agctacatat tgcagaagag tacatttgaa gtgcctgaaa ccagatgact atcttaaaga        480
ctgttaaggg cgaattc                                                      497

<210> SEQ ID NO 7
<211> LENGTH: 122
<212> TYPE: DNA
<213> ORGANISM: Homo sapiens
<220> FEATURE:
<221> NAME/KEY: human brca1 exon11
<222> LOCATION: (1)..(122)
<223> OTHER INFORMATION: part of human brca1 exon11 seqence from
      genbank.

<400> SEQUENCE: 7
tgcttgtgaa ttttctgaga cggatgtaac aaatactgaa catcatcaac ccagtaataa        60
tgatttgaac accactgaga agcgtgcagc tgagaggcat ccagaaaagt atcagggtag       120
tt                                                                     122

<210> SEQ ID NO 8
<211> LENGTH: 127
<212> TYPE: DNA
<213> ORGANISM: Homo sapiens
<220> FEATURE:
<221> NAME/KEY: human brca1 exon11
<222> LOCATION: (1)..(122)
<223> OTHER INFORMATION: PCR product sequence , part of human brca1
      exon11 from human blood genomic DNA

<400> SEQUENCE: 8
tgcttgtgaa ttttctgaga cggatgtaac aaatactgaa catcatcaac ccagtaataa        60
tgatttgaac accactgaga agcgtgcagc tgagaggcat ccagaaaagc atcggggtag       120
ttctgtt                                                                127
```